US006551293B1

(12) United States Patent
Mitchell

(10) Patent No.: US 6,551,293 B1
(45) Date of Patent: Apr. 22, 2003

(54) EXTERNAL MALE URINARY CATHETER ASSEMBLY AND METHOD

(76) Inventor: George V. Mitchell, 7160 E. Fouch Rd., Traverse City, MI (US) 49684-7530

( * ) Notice: Subject to any disclaimer, the term of this patent is extended or adjusted under 35 U.S.C. 154(b) by 13 days.

(21) Appl. No.: 09/931,460

(22) Filed: Aug. 16, 2001

(51) Int. Cl.[7] .................................................. A61F 5/44
(52) U.S. Cl. ...................... 604/353; 604/327; 604/346; 604/347; 604/349; 604/351; 604/355
(58) Field of Search ................................ 604/327, 346, 604/347, 348, 349, 350, 351, 353, 355

(56) References Cited

U.S. PATENT DOCUMENTS

| | | | |
|---|---|---|---|
| 2,445,220 A | 7/1948 | Isaacson | |
| 2,873,740 A | 2/1959 | Wainwright | |
| 3,526,227 A | 9/1970 | Appelbaum | |
| 3,585,997 A | * 6/1971 | Ancerewicz, Jr. | 604/327 |
| 4,387,726 A | * 6/1983 | Denard | 600/573 |
| 4,534,768 A | 8/1985 | Osburn et al. | |
| 4,553,968 A | 11/1985 | Komis | |
| 4,568,340 A | 2/1986 | Giacalone | |
| 4,588,397 A | 5/1986 | Giacalone | |
| 4,673,401 A | * 6/1987 | Jensen et al. | 604/353 |
| 4,713,066 A | 12/1987 | Komis | |
| 4,813,943 A | * 3/1989 | Smith | 604/329 |
| 4,994,051 A | * 2/1991 | Walsh | 604/349 |
| 5,013,308 A | 5/1991 | Sullivan et al. | |
| 5,346,483 A | 9/1994 | Thaxton, Sr. | |
| 5,409,475 A | * 4/1995 | Steer | 604/353 |
| 5,411,495 A | * 5/1995 | Willingham | 604/329 |
| 5,423,785 A | * 6/1995 | Hart | 604/353 |
| 5,439,456 A | * 8/1995 | Fabricant | 604/327 |
| 5,478,334 A | * 12/1995 | Bernstein | 604/353 |
| 5,520,671 A | 5/1996 | Bouser | |
| 5,593,389 A | 1/1997 | Chang | |
| 5,616,138 A | 4/1997 | Propp | |
| 5,645,541 A | 7/1997 | Bouser | |
| 5,649,913 A | * 7/1997 | Cohen | 604/353 |
| 6,007,524 A | 12/1999 | Schneider | |
| 6,010,489 A | * 1/2000 | Blackburn | 604/353 |
| 6,059,762 A | 5/2000 | Boyer et al. | |
| 6,409,971 B1 | * 6/2002 | Wilkinson et al. | 422/103 |
| 2002/0104148 A1 | * 8/2002 | Silverman | 2/48 |
| 2002/0177825 A1 | * 11/2002 | Scovel | 604/353 |

* cited by examiner

*Primary Examiner*—Weilun Lo
*Assistant Examiner*—Michael Bogart
(74) *Attorney, Agent, or Firm*—Reising, Ethington, Barnes, Kisselle, Learman & McCulloch, P.C.

(57) ABSTRACT

The external male urinary catheter assembly has a flexible moisture barrier sheet with a penis passage. The penis passage has a plurality of flaps, separated by radial slots. These slots are extended outward to adjust passage diameter. A liquid absorbent material pad has an absorbent material pad passage that is coaxial with the penis passage. A cup member has an inlet end flange that is held in alignment with the penis passage by a harness plate and harness. The absorbent material pad is compressed between the cup member flange and the moisture barrier sheet. The absorbent material pad absorbs liquid that is adjacent to the penis passage as well as liquid that passes between the cup flange and the moisture barrier.

13 Claims, 2 Drawing Sheets

EXTERNAL MALE URINARY CATHETER ASSEMBLY AND METHOD

TECHNICAL FIELD

The external male urinary catheter collects liquids from the urinary tract of a male and protects a male's skin from urinary catheter leakage.

BACKGROUND OF THE INVENTION

Male Homosapiens may develop a number of different medical conditions that require surgery in the lower portion of the trunk. Such surgery may affect the urinary track and organs connected to or associated with the urinary track. These effects may include swelling and or urinary tract drainage. The fluids that drain from the urinary tract following surgery can be very caustic. Upon contact between such drainage and the skin of the legs or lower trunk, a burning sensation is frequently experienced. Extreme pain may accompany the burning sensation.

External male urinary catheters are available which can keep drainage from the urethra from contact with all exposed skin except skin on the penis. Unfortunately these catheters are not useable when the drainage is accompanied by swelling or soreness of the penis. Urinary catheters that can be used when there is swelling or soreness generally permit at least some leakage from time to time that contacts the skin. This contact between the skin and caustic drainage can cause unacceptable pain.

SUMMARY OF THE INVENTION

The external male urinary assembly has a flexible moisture barrier sheet with a penis passage. A liquid absorbent material pad is adjacent to the flexible barrier sheet with an absorbent material pad passage generally coaxial with the penis passage. A cup member has cup member flange that extends radially outward from a large diameter opening on an inlet end of the cup member. A cup member discharge opening is provided in the cup member. The liquid absorbent material pad is compressed between the flexible moisture barrier sheet and the cup member flange. A first portion of the liquid absorbent material pad extends radially outward from the cup member flange. A harness engages the cup member and holds the cup member, the liquid absorbent material pad, and the flexible moisture barrier sheet in position to receive urinary drainage. A liquid holding container is connected to the cup member discharge opening by a flexible discharge tube.

BRIEF DESCRIPTION OF THE DRAWINGS

The presently preferred embodiment of the invention is disclosed in the following description and in the accompanying drawings, wherein.

DESCRIPTION OF THE PREFERRED EMBODIMENT

Figure 1:
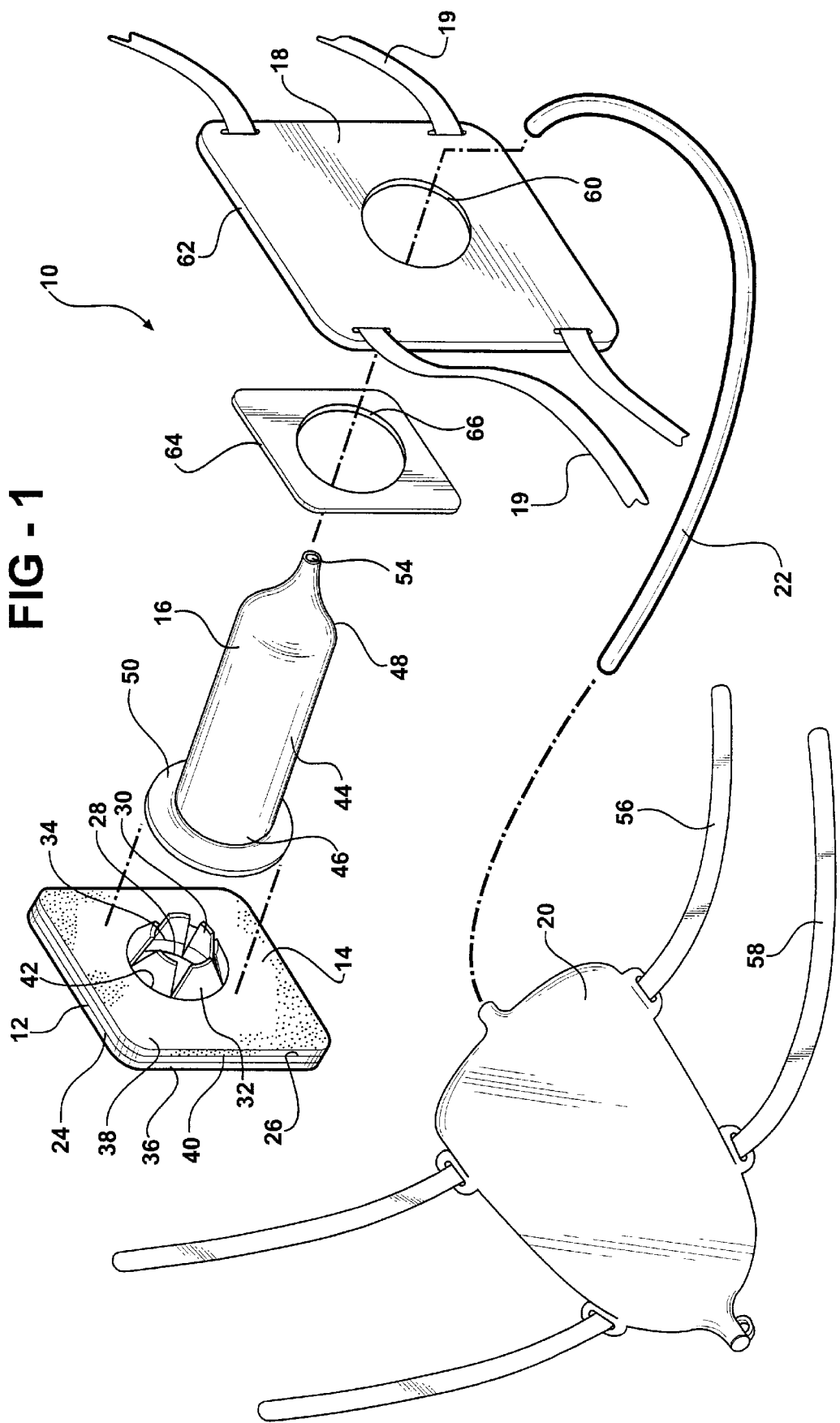
FIG. 1 is an expanded view of the external male urinary catheter assembly.

The external male urinary catheter assembly 10 includes a flexible moisture barrier sheet 12, a liquid absorbent material pad 14, a cup member 16, a harness plate 18 and a harness 19. A liquid holding bag 20 can be attached to the cup member 16 by flexible tube 22 if desired.

The flexible moisture barrier sheet 12 is a thin plastic or rubber sheet with an inside surface 24 that faces toward a user of the urinary catheter 10 and an outside surface 26 that faces away from the user. A penis passage 28 is formed in the moisture barrier sheet 12 by cutting a plurality of radial slots 30 and forming a plurality of flaps 32. By cutting the slots 30 at the time of use or extending the slots radially outward if short radial slots 30 are precut, the diameter of the penis passage 28 can be held to a minimum acceptable size thereby obtaining a relatively snug fit. By providing a small penis passage 28 that is increased in diameter at the time of use, the user can accommodate swelling, changes in swelling and biological differences between different users as well as day to day changes in a user's requirements and thereby obtain an acceptable fit. The process of cutting the slots 30 in the moisture barrier sheet 12 can be simplified by marking concentric circles 34 (only one is shown) with different diameters on the sheet which can be used as a guide to determine how far to extend the slots.

Plastic and rubber, when in direct contact with skin, keep air from the skin, hold perspiration against the skin, increase skin temperature and are often uncomfortable. Some individuals are also allergic to rubber. These problems associated with plastic and rubber can be avoided by laminating a cotton sheet 36 or a similar fibrous material to the inside surface 24 of the moisture barrier sheet 12. The fiber sheet 36 is shown in FIG. 1 only.

The liquid absorbent pad 14 has an absorbent material outside surface 38 and an absorbent material inside surface 40. An absorbent material pad passage 42 through the pad 14 is substantially coaxial with the penis passage 28 through the moisture barrier sheet 12. As shown, the absorbent pad 14 is bonded to the moisture barrier sheet 12 to form a laminate. If desired the barrier sheet 12 could be a separate piece from the absorbent pad 14. For the barrier sheet 12 to be a separate piece, it would need to be semi-flexible. The absorbent pad 14 and the moisture barrier sheet 12, as shown in the drawing figures are flat members. Comfort and fit can be improved by molding the sheet 12 and the absorbent pad 14 to conform to the shape of the portion of the human body they contact during use. If the sheet 12 and absorbent pad 14 are not molded, they should have sufficient flexibility even when they are laminated to conform to the shape of the user. The absorbent pad 14 can be made from a number of different materials. The materials employed on the inside of some disposable diapers would work well.

The cup member 16 has a tubular body 44 with an inlet end 46 and an outlet end 48. The cup member flange 50 extends radially outward from the inlet end 46 of the tubular body 44 and defines a large diameter opening 52. A discharge passage 54 is provided in the outlet end 48 of the tubular body 44. The cup member 16 has an inside diameter that is at least as large as the diameter of a swollen penis P so that there is no resistance to inserting the penis into the cup. The cup member 16 is flexible so that it can be positioned to provide comfort for a person employing the catheter assembly 10. Flexibility also permits the discharge passage 54 to move to a position as low as or below the remainder of the cup member 16 to facilitate the free flow of discharged liquids through the discharge passage.

Figure 2:
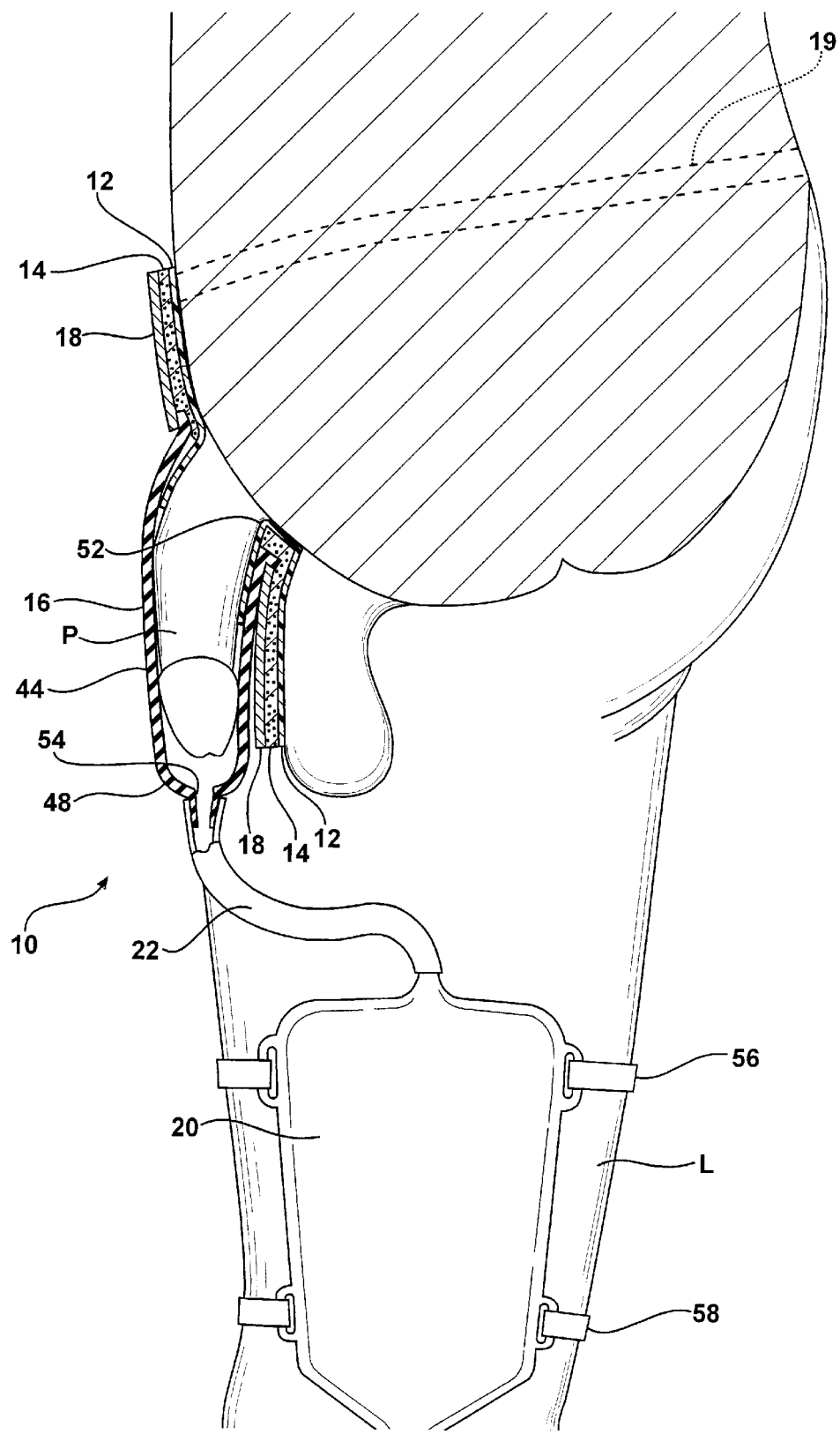
FIG. 2 is a sectional view of the urinary catheter in use with parts broken away.

The liquid holding bag 20 is connected to the discharge passage 54 by a flexible tube 22. The straps 56 and 58 are provided to attach the holding bag 20 to the leg L of a person. The holding bag 20 is shown attached to the inside portion of the leg L in FIG. 2. In practice, the holding bag 20 is normally attached to the outside portion of a person's leg L to facilitate walking. While a person is in bed, it is generally desirable to attach the holding bag 20 to the bed frame or other support structure that supports the holding bag below the upper surface of the mattress to ensure liquid flow through the tube 22 and into the holding bag.

The harness plate 18 has a harness plate aperture 60 that telescopically receives the tubular body 44 of the cup member 16. An inside surface 62 of the harness plate 18 engages the cup member flange 50 and urges the cup member flange toward the absorbent material pad 14. Portions of the absorbent material pad 14 adjacent to the absorbent material pad passage 42 are compressed between the cup flange 50 and the moisture barrier sheet 12 to form a seal.

A spacer 64 with a central bore 66, shown in FIG. 1 only, can be employed if needed. The central bore 66 telescopically receives the tubular body 44 of the cup member 16 and contacts the cup member flange 50 and the harness plate inside surface 62. In this position, the spacer 64 increases the force on the flange 50 to improve the seal between the flange and the moisture barrier sheet 12. The spacer 64 also provides more space for the portions of the liquid absorbent material pad 14 that extend radially outward from the cup member flange 50. The additional space permits the pad 14 to absorb and hold more liquid than it could hold if it were compresses into a smaller space.

Portions of the liquid absorbent material pad 14 that extends radially inward from the cup member flange 50 tends to absorb liquid drainage that moves into the area adjacent to the large diameter opening 52 of the cup member 16. Occasionally due to the position of a person using the catheter assembly 10, some drainage liquid may move up toward the large diameter opening 52. Such liquid will be absorbed by the absorbent material pad 14 and will not pass through the penis passage 28. The radial slots 30 tend to direct drainage liquid to the absorbent material pad 14. The liquid that is absorbed by portions of the absorbent material pad 14 inside the cup member 16 will be slowly absorbed by portions of the pad that are compressed by the cup member flange 50 and then by portions of the pad that extend radially outward from the cup member flange.

The disclosed embodiment is representative of a presently preferred form of the invention, but is intended to be illustrative rather than definitive thereof. The invention is defined in the claims.

What is claimed is:

1. An external urinary catheter assembly comprising:
   a flexible moisture barrier sheet with a penis passage;
   a liquid absorbent material pad adjacent to the flexible barrier sheet and having an absorbent material pad passage that is generally coaxial with a penis passage;
   a cup member with a cup member flange that extends radially outward from a large diameter opening on an inlet end of the cup member, a cup member discharge opening in the cup member, and wherein the liquid absorbent material pad is compressed between the flexible moisture barrier sheet and the cup member flange and a first portion of the liquid absorbent material pad extends radially outward from the cup member flange;
   a harness that engages the cup member and holds the cup member, the liquid absorbent material pad, and the flexible moisture barrier sheet in position to receive urinary drainage; and
   a liquid holding container connected to the cup member discharge opening by a flexible discharge tube.

2. An external male urinary catheter assembly, as set forth in claim 1, wherein in the penis passage through the moisture barrier sheet has a diameter that is enlargable.

3. An external male urinary catheter assembly, as set forth in claim 1, wherein the penis passage through the moisture barrier sheet includes a plurality of generally radially extending slots in the moisture barrier sheet that are extendable radially outward to increase the diameter of the penis passage.

4. An external male urinary catheter assembly, as set forth in claim 3, including at least one circular arc on the moisture barrier sheet that is concentric with the penis passage and serves as a guide for extending the plurality of generally radially extending slots.

5. An external male urinary catheter assembly, as set forth in claim 1, wherein a second portion of the liquid absorbent material pad extends radially inward from the cup member flange.

6. An external male urinary catheter assembly as set forth in claim 1, including a harness plate with a harness plate aperture that telescopically receives a discharge end of the cup member and wherein the harness is attached to the harness plate.

7. An external male urinary catheter assembly, as set forth in claim 6, including a spacer with a spacer bore that telescopically receives the discharge end of the cup member and wherein the spacer is positioned between the cup member flange and the harness plate and transfers force from the harness plate to the cup member flange to compress the liquid absorbent material pad between the cup member flange and the flexible moisture barrier sheet.

8. An external male urinary catheter assembly, as set forth in claim 1, wherein the liquid absorbent material pad is attached to the flexible moisture barrier sheet by an adhesive.

9. An external male urinary catheter assembly, as set forth in claim 1, wherein the flexible moisture barrier sheet has an outside barrier surface facing the liquid absorbent material pad, an inside barrier surface, and a cotton sheet secured to the inside barrier surface.

10. An external male urinary catheter assembly comprising:
    a flexible moisture barrier sheet with an inside barrier sheet surface, an outside barrier sheet surface, a penis passage having a plurality of flaps separated by a radial slot between each pair of adjacent flaps and wherein the radial slots are cut to a selected length to obtain a selected penis passage diameter;
    a liquid absorbent material pad with an absorbent material outside surface and an absorbent material inside surface and wherein the absorbent material inside surface faces the outside barrier sheet surface, an absorbent material pad passage generally coaxial with the penis passage through the flexible moisture barrier sheet and wherein the absorbent material pad passage receives the plurality of flaps;
    a cup member with a cup member flange that extends radially outward from a large diameter opening on an inlet end of the cup member, and a cup member discharge opening in the cup member;
    a harness plate with a harness plate central aperture that telescopically receives the cup member and engages the cup member flange;
    a harness connected to the harness plate that supports the harness plate and urges the harness plate toward the flexible moisture barrier sheet and compresses the liquid absorbent material pad between the harness plate and the outside barrier sheet surface and forms a seal between the cup member flange and the outside barrier sheet surface; and a liquid holding bag connected to the cup member discharge opening by a flexible discharge tube.

11. An external male urinary catheter assembly, as set forth in claim 10, including a spacer with a spacer bore that telescopically receives a discharge end of the cup member and wherein the spacer is positioned between the cup member flange and the harness plate.

12. An external male urinary catheter assembly, as set forth in claim 11, wherein the spacer transfers force from the harness plate to the cup member flange to compress the liquid absorbent material between the cup member flange and the flexible moisture barrier sheet.

13. An external male urinary catheter assembly, as set forth in claim 10, including a sheet of fibrous material secured to the inside barrier sheet surface.

* * * * *